Figure 1:
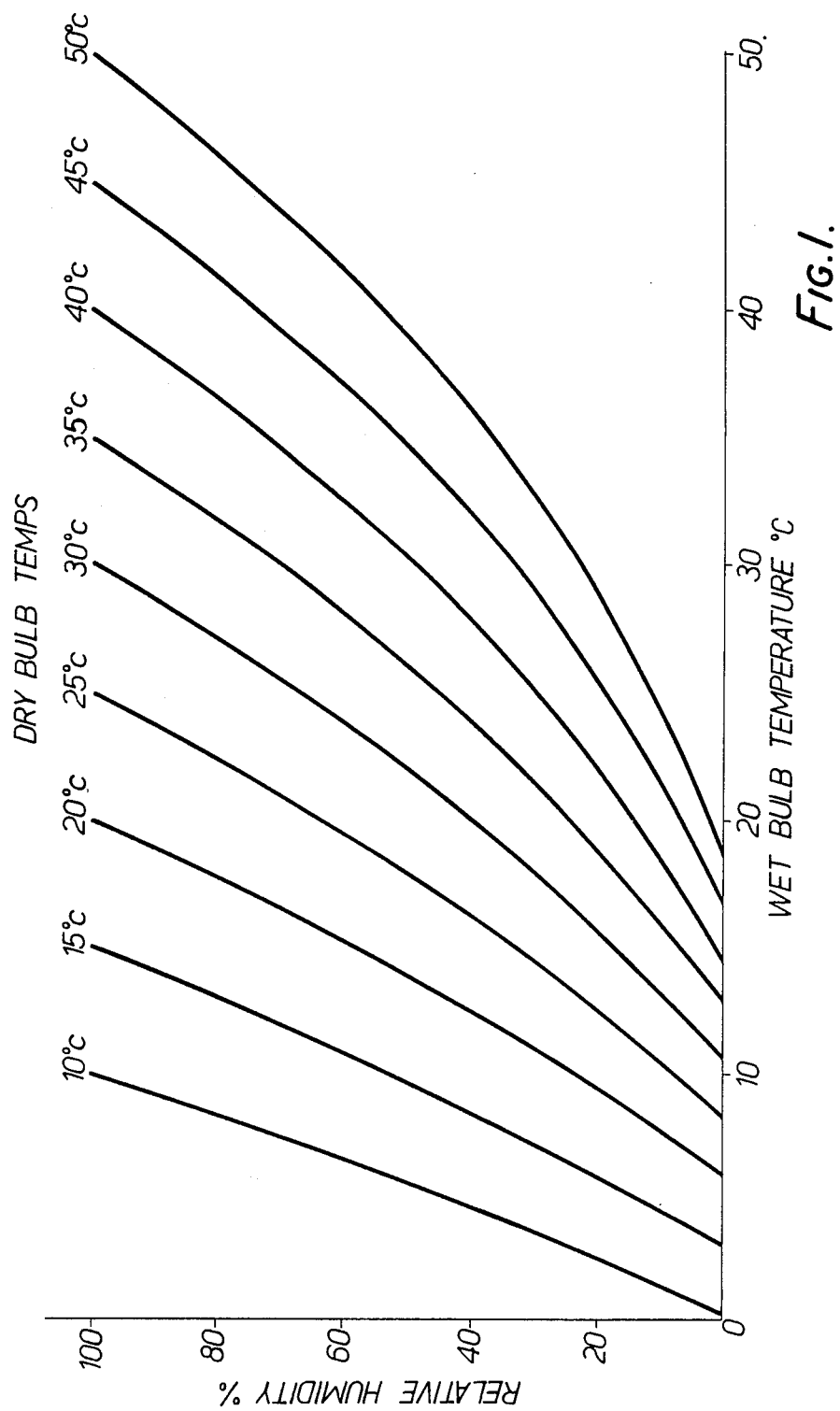

United States Patent [19]

de Yong

[11] Patent Number: 4,872,340
[45] Date of Patent: Oct. 10, 1989

[54] PSYCHROMETER

[75] Inventor: John L. de Yong, Victoria, Australia

[73] Assignee: Commonwealth Scientific and Industrial Research Organization, Campbell, Australia

[21] Appl. No.: 294,642

[22] Filed: Aug. 20, 1981

[30] Foreign Application Priority Data

Aug. 22, 1980 [AU] Australia ............................. PE5203

[51] Int. Cl.$^4$ ........................ G01N 25/64; G01N 1/06
[52] U.S. Cl. ..................................... 73/338; 73/336.5
[58] Field of Search .................... 73/336.5, 338, 338.3, 73/338.6

[56] References Cited

U.S. PATENT DOCUMENTS 2,915,898 12/1959 Van Luik ........................... 73/338.3
3,886,797  6/1975 Bauer ................................... 73/338
3,894,434  7/1975 Flam .................................... 73/338

OTHER PUBLICATIONS

Wet/Dry Bulb Thermistor Hygrometer with Digital Indication; Atkins; Apr. 1964; Instruments & Control Systems, pp. 111-114.
Direct Indication Psychrometer of Temperature-Diference and Temperature Type; Schiba; July 1978, pp. 635(19), 640(24).
The Precise Measurement of Relative Humidity in Paper Testing Rooms; de Yong (vol. 29, No. 3, pp. 174-179), Digital Ventilate D-Psychrometer; Nantou; IEEE Transactions on Instrumentation and Measurement; Mar. 1979.
Digital Ventilated Psychrometer; by Nantou; IECE Transactions of Japan; vol. EG1, No. 8, Aug. 1978, Abstracts.

Primary Examiner—William A. Cuchlinski Jr.
Assistant Examiner—Patrick R. Scanlon
Attorney, Agent, or Firm—Sughrue, Mion, Zinn, Macpeak & Seas

[57] ABSTRACT

A psychrometer having transducers producing two electrical signals respectively representing dry bulb temperature and wet bulb temperature, and an electrical circuit operating to derive a signal representing relative humidity in accordance with the formula:

$$RH = \frac{\alpha + \beta t + \gamma t'}{\alpha' + \beta' t + \gamma' t'}$$

where
 RH is the relative humidity
 t is the dry bulb temperature
 t' is the web bulb temperature and
 $\alpha, \beta, \gamma, \alpha', \beta'$, and $\gamma'$ are constants.
The constants are chosen to give accurate results over the desired operating range of the psychrometer.
Suitable values for many applications are:

$\alpha = 10.5 \quad \alpha' = 9$
$\beta = -1 \quad \beta' = 2.2$
$\gamma = 2 \quad \gamma' = -1.2$ 4 Claims, 2 Drawing Sheets

PSYCHROMETER

This invention relates to psychrometers, and is an improvement in the psychrometer described at pages 175 to 179 of the November 1975 issue (Volume 29 No. 3) of "Appita" (The Journal of the Australian and New Zealand Pulp and Paper Industry Technical Association).

A known method of measuring relative humidity is based on the principle that the rate of evaporation of water from a wet surface, and hence the cooling of that surface, is dependent on the level of water vapour in the surrounding air. An instrument using this technique is known as a wet and dry bulb psychrometer. The "wet and dry bulb" refers to the two thermometers used, one with the bulb bare, and hence measuring the air temperature, and the other covered with a wet sleeve, usually of woven cotton, which is kept wet by capillary action from a water reservoir, hence measuring the cooling effect. This cooling effect measured by the difference between dry bulk temperature and wet bulb temperature is referred to as the wet bulb depression.

The following relationship, known as the psychrometric equation, is widely used to obtain relative humidity (RH) values from wet bulb and dry bulb temperatures:

$$RH = \frac{e' - aP(t - t')(1 + bt')}{e} \times 100 \text{ percent} \tag{1}$$

where $e'$ is the saturation vapour pressure of water at the wet bulb temperature $t'$ $e$ is the saturation vapour pressure of water at the dry bulb temperature $t$ $a$ is the psychrometric coefficient $P$ is the atmospheric pressure $t$ is the dry bulb temperature $t'$ is the wet bulb temperature The $(1+bt')$ term is close to unity as "b" is a small value constant, and hence this term is often omitted.

To calculate relative humidity, values of "e" and "e'" must be obtained from vapour pressure tables for substitution in equation (1). Alternatively, graphs or tables relating relative humidity, dry bulb temperature, and either wet bulb temperature or wet bulb depression may be prepared in accordance with equation (1). Such tables are used with psychrometers which employ mercury-in-glass thermometers.

As a first approximation we have found that it is possible to model the relationship between relative humidity and wet and dry bulb temperature by an equation of the form:

$$RH = \frac{A + (B + aP)t' - aPt}{A + Bt} \tag{2}$$

where "A", "B" and "a" are constants.

For each value assigned to "t", this equation gives a straight line graphs of relative humidity versus $t'$. However, graphs of relative humidity versus $t'$ derived from the basic psychrometric equation have the form of a family of curves (see FIG. 1). To better fit such curves, two empirical modifications may be made to the above equation.

1. the coefficients can be adjusted for optimum fit at the extremes of relative humidity required i.e. 0% and 100%
2. a term, preferably linear, may be added to the denominator to approximate the required curvature of the graphs.

This leads to an equation of the form $$RH = \frac{A' + (B' + aP)t' - aPt}{A'' + B't + Dt'} \tag{3}$$

where A', B', a, A" and D are constants.
or more generally stated $$RH = \frac{\alpha + \beta t + \gamma t'}{\alpha' + \beta' t + \gamma' t'} \tag{4}$$

where $\alpha, \beta, \gamma, \alpha', \beta'$, and $\gamma'$ are constants.

Generally, the invention provides a psychrometer comprising first means for providing a first electrical signal representative of dry bulb temperature, second means for providing a second electrical signal representative of wet bulb temperature, and signal processing means coupled to said first and second means to in use provide an output signal representative of the relative humidity in accordance with any one of equations 2, 3 or 4 above.

In its most preferred form, the invention provides a psychrometer comprising first means for providing a first electrical signal representative of dry bulb tempeature, second means for providing a second electrical signal representative of wet bulb temperature, and signal processing means coupled to said first and second means to in use provide an output signal representative of the relative humidity in accordance with the following equation:

$$RH = \frac{\alpha + \beta t + \gamma t'}{\alpha' + \beta' t + \gamma' t'}$$

where:
RH is the relative humidity
$\alpha, \beta, \gamma, \alpha', \beta', \gamma'$ are constants
t is the dry bulb temperature
t' is the wet bulb temperature Preferably said first and second means in use generate said first and second signals as analogue signals and said signal processing means in use receives and processes said first and second signals by analogue processing to produce said output signal as an analogue signal.

The signal processing means may comprise numerator means in use generating the numerator of said equation, denominator means in use generating the denominator of the said equation, and divider means in use generating the said output signal by division of output from said numerator means by the output of said denominator means.

The numerator means preferably includes a first inverter connected to in use receive said second signal and a first summing amplifier of the kind in which signals are presented for summing to a first common junction via respective resistors selected to weight the so presented signals, said first junction being connected via first, second and third resistors respectively to a source of fixed negative voltage, the output of said first means, and to the output of said first inverter, whereby the constants α, β, and γ are determined in accordance with the values of said first, second and third resistors respectively.

The denominator means preferably comprises a second inverter connected to in use receive output from said first means and a second summing amplifier of the kind in which signals are presented for summing to a second common junction via respective resistors selected to weight the so presented signals, said second junction being connected via fourth, fifth and sixth resistors respectively to a source of fixed negative voltage, the output of said second inverter, and to the output of said second means, whereby the constants α', β', γ' are determined in accordance with respective values of the fourth, fifth and sixth resistors.

The aforementioned constants α, β, γ, α', β', γ' may have values as follows:

$$\alpha = 10.5 \quad \alpha' = 9$$
$$\beta = -1 \quad \beta' = 2.2$$
$$\gamma = 2 \quad \gamma' = -1.2$$

Of course, the invention could be implemented by means other than analogue circuitry, such as by digital circuitry or by use of a microprocessor or other computing apparatus.

Figure 2:
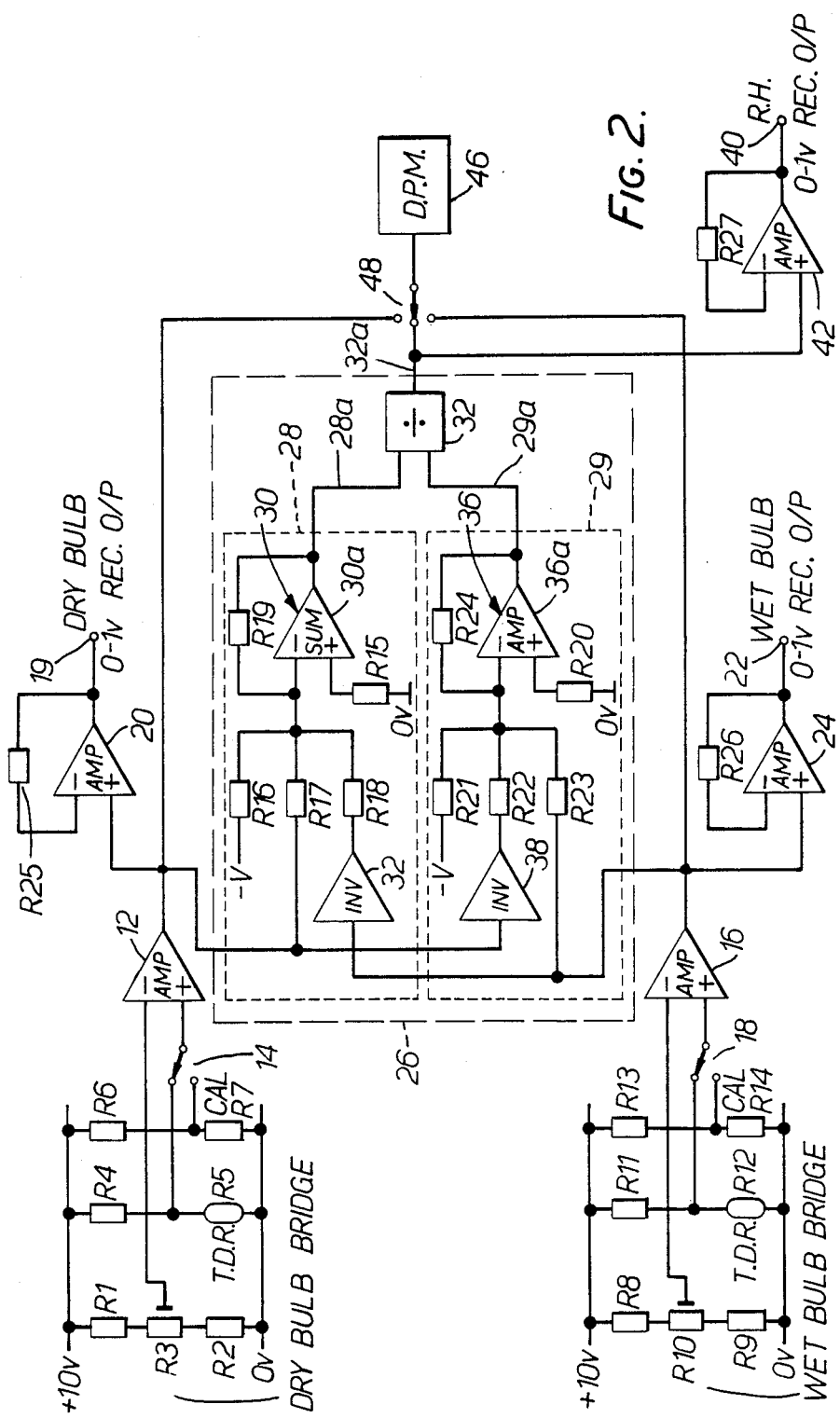

The invention is further described by way of example with reference to the accompanying drawings in which:

FIG. 1 is a graph of relative humidity versus wet bulb temperature for various dry bulb temperatures; and FIG. 2 is a circuit diagram of a psychrometer constructed in accordance with the invention.

The circuit of FIG. 2 is that of a pschrometer which generates an output signal representative of relative humidity in accordance with the following equation:

$$RH = \frac{\alpha + \beta t + \gamma t'}{\alpha' + \beta' t + \gamma' t'} \quad (4)$$

As mentioned, this provides a means of approximating the family of curves of relative humidity versus wet bulb temperature for various dry bulb temperatures, as shown in FIG. 1.

The circuit of FIG. 2 is operated from a dc power supply (not shown). The circuit includes a dry bulb bridge made up of two series chains of resistors. The first of these chains comprises a resistor R1 connected to positive supply, a resistor R2 connected to ground and a third, variable, resistor R3 interconnected as a voltage divider between resistors R1 and R2.

The other chain comprises two series connected resistors R4 and R5, resistor R5 being a temperature dependent resistor. Output is taken from the movable contact of resistor R3 to the inverting terminal of a differential amplifier 12 and from the junction of resistors R4 and R5 to the non-inverting input of amplifier 12. A switch 14 is interposed between the junction between resistors R4 and R5 and the non-inverting terminal of amplifier 12 so as to selectively permit switching of the non-inverting input of amplifier 12 away from the junction between resistors R4 and R5 and to the junction of two series resistors R6 and R7 between positive supply and ground, for the purposes of calibration. A wet bulb bridge is also provided made up of two resistor chains connected in parallel between positive supply and ground. The first of these chains comprises resistor R8 connected to positive supply and resistor R9 connected to group, these resistors being interconnected by variable resistor R10. The second chain comprises two series connected resistors R11 and R12, resistor R12 being a temperature dependent resistor. Output from the bridge is taken from the movable contact of resistor R10 and from the junction between the resistors R11 and R12 to a differential amplifier 16. The line from the junction between resistors R11 and R12 to the non-inverting input of amplifier 16 includes a switch 18 to enable switching of the non-inverting input away from the junction between resistors R11 and R12 to a junction between two series connected resistors R13 and R14 connected between positive supply and ground, for calibration purposes.

The temperature dependent resistors R5 and R12 comprise the temperature sensing thermometers for the psychrometer. These are platinum resistance elements. The elements are provided in respective very thin-walled stainless steel tubes fixed across a square duct, the interior of which is painted matt black and through which air is drawn at a suitable velocity by a small axial fan. The surface of the tube housing the dry bulb temperature sensing element is simply exposed to the air flow and an arrangement is provided for wetting the surface of the wet bulb element. This may, for example, be effected by covering the wet bulb tube with a wet wick of suitable woven material such as cotton or rayon, one end of which dips into a water reservoir outside the duct.

The output from the differential amplifier 12 is proportional to the voltage difference between the movable contact of resistor R3 and the junction between resistors R4 and R5 and thus exhibits progressive variation in accordance with the temperature of air drawn through the psychrometer duct. The output of differential amplifier 16 is proportional to the difference in voltage between the movable contact of resistor R10 and the junction between resistors R11 and R12 and is proportional to wet bulb temperature. Provision is made for obtaining direct readout of these amplifier outputs. Thus, a terminal 19 at which a voltage representative of dry bulb temperature appears is interconnected with the output from amplifier 12 by a buffer amplifier 20 and its associated feedback resistor R25. Similarly, a terminal 22 at which an output representative of the wet bulb temperature appears is interconnected with the output of amplifier 16 via a buffer amplifier 24 and its associated feedback resistor R26. Generation of an output voltage representative of relative humidity is effected by a signal processing circuit 26 including a numerator determining circuit 28, a denominator determining circuit 29 and a divider 32. Numerator determining circuit 28 comprises a summing amplifier 30, formed by an operational amplifier 30a having its non-inverting input connected to ground via a resistor R15 and its inverting input connected to the output via a feedback resistor R19. The inverting input receives three signals to be summed via respective resistors R16, R17, R18. Resistor R16 is connected between the inverting input of amplifier 30a and a fixed negative voltage. Resistor R17 is connected between the inverting input of amplifier 30a and the output from amplifier 12. Resistor R18 is connected between the inverting input of amplifier 30a and the output of inverter 32 which in turn receives output from amplifier 16.

Denominator determining circuit 29 includes a summing amplifier 36 formed from an operational amplifier 36a having its inverting input connected to the output via a feedback resistor R24 and its non-inverting input connected to ground via a resistor R20. The inverting input of amplifier 36a receives signals via three resistors R21, R22, R23. Resistor R21 is connected between the inverting input of amplifier 36a and a fixed negative voltage. Resistor R22 is connected between the inverting input of amplifier 36a and the output of inverter 38 which in turn receives output from amplifier 12. Resistor R23 is connected between the inverting input of amplifier 36a and the output from amplifier 16.

The resistors R16, R17, R18 and R19 are chosen to in use modify the input signal voltages to amplifier 30a by the respective constants $\alpha$, $\beta$, and $\gamma$ in equation (4) above and resistors R1, R22, R23 and R24 are chosen to modify the input signal voltages to amplifier 36a by the respective constants $\alpha'$, $\beta'$, and $\gamma'$. Since resistor R16 is connected to a fixed negative supply voltage, the voltage developed thereacross is representative of the term $-\alpha$. Since R17 is connected to the output of amplifier 12, the voltage developed thereacross is representative of the term $\beta t$. The resistor R18, being connected to the output of amplifier 16 via inverter 32, generates thereacross a voltage representative of the term $-\gamma t'$, the sign of this term being negative because of inverter 32. Similarly, the resistor R21, being connected to a fixed negative supply voltage, develops thereacross a voltage representative of the term $-\alpha'$. The resistor R22, being connected to amplifier 12 via inverter 38, develops thereacross a voltage representative of the term $-\beta' t$, the sign of this term being negative because of the inverter 38. Lastly, the resistor R23 being connected to amplifier 16, develops thereacross a voltage representative of the term $\gamma' t'$. The voltage developed across resistors R16, R17 and R18 are summed and inverted by amplifier 30 and presented on an output line 28a to divider 32. The voltages appearing across resistors R21, R22 and R23 are summed and inverted by amplifier 36 and presented on an output line 29a to divider 32. The output on line 28a thus comprises the summation $\alpha + \beta t + \gamma t'$ and that on line 29a the summation $\alpha' + \beta' t + \gamma' t'$, the signs of $\beta$ and $\gamma$ being made negative by inversion in the summing amplifiers 30 and 36 respectively. The divider effects division of the numerator terms by the denominator terms and presents an output signal representative of the division at an output 32a. Output from divider 32 may, for example, be taken to a recording output terminal 40 via a suitable buffer amplifier 42 and its associated feedback resistor R27. This output directly represents relative humidity.

A suitable formof digital panel-meter 46 may also be incorporated, this having an input switchable, by means of a switch 48, to receive output selectively either from amplifier 12, from divider 32 or from amplifier 16 to give read-out, selectively, of the corresponding dry bulb temperature, a computation of relative humidity, or wet bulb temperature.

The described arrangement has been advanced merely by way of explanation. In practice, the values of the resistors R16, R17, R18, R19, R21, R22, R23 and R24 are selected in order to provide an optimum fit for modelling the desired relationship between the variables t and t', inverters being provided where reversal of sign is necessary. Thus, the positioning of inverters and the values of resistors R16, R17, R18, R19, R21, R22, R23 and R24 may be selected to give the following numerical values for the constants:

$$\alpha = 10.5 \quad \alpha' = 9$$
$$\beta = -1 \quad \beta' = 2.2$$
$$\gamma = 2 \quad \gamma' = -1.2$$

However, depending on the range over which measurement is required, and other variables, it may be necessary to depart from these values.

Of course, the best values for the constants $\alpha$, $\beta$, $\gamma$, $\alpha'$, $\beta'$, $\gamma'$ will vary with the range of relative humidity and temperature over which the equation is required to function, as will the accuracy of the approximation represented by the equation. However, typically, over the range 0° to 50° C. dry bulb temperature and using the values for the constants tabulated above, an accuracy of ±2.5% relative humidity has been found to be achievable between 20% and 90% relative humidity. By restricting the dry bulb temperature to the range 20° to 50° C. the accuracy is improved to be ±1.5% for the same values of the constants.

I claim:

1. A psychrometer comprising first means for providing a first electrical signal representative of dry bulb temperature, second means for providing a second electrical signal representative of wet bulb temperature, and signal processing means coupled to said first and second means to in use provide an output signal representative of the relative humidity in accordance with the equation:

$$RH = \frac{\alpha + \beta t + \gamma t'}{\alpha' + \beta' t + \gamma' t'}$$

where
RH is the relative humidity
t is the dry bulb temperature
T' is the wet bulb temperature,
and
$\alpha$, $\beta$, $\gamma$, $\alpha'$, $\beta'$, and $\gamma'$ are constants;
wherein said signal processing means comprises numerator means in use generating the numerator of said equation, denominator means in use generating the denominator of said equation, and divider means in use generating the said output signal by division of output from said numerator means by the output of said denominator means, and
wherein said numerator means includes a first inverter connected to in use receive said second signal and a first summing amplifier of the kind in which signals are presented for summing to a first common junction via respective resistors selected to weight the so presented signals, said first junction being connected via first, second and third resistors respectively to a source of fixed negative voltage, the output of said first means, and to the output of said first inverter, whereby the constants $\alpha$, $\beta$ and $\gamma$ are determined in accordance with the values of said first, second and third resistors respectively.

2. A psychrometer as claimed in claim 1 wherein said denominator means comprises a second inverter connected to in use receive output from said first means and a second summing amplifier of the kind in which signals are presented for summing to a second common junction via respective resistors selected to weight the so presented signals, said second junction being connected via fourth, fifth and sixth resistors respectively to a source of fixed negative voltage, the output of said second inverter, and to the output of said second means, whereby the constants $\alpha'$, $\beta'$, and $\gamma'$ are determined in accordance with respective values of the fourth, fifth and sixth resistors.

3. A psychrometer as claimed in claim 2, wherein said constants $\alpha$, $\beta$, $\gamma$, $\alpha'$, $\beta'$, $\gamma'$ have values substantially as follows:

$\alpha = 10.5$  $\alpha' = 9$
$\beta = -1$  $\beta' = 2.2$
$\gamma = 2$  $\gamma' = -1.2$ 4. A psychrometer as claimed in claim 1, wherein said first and second means in use generate said first and second signals as analogue signals and said signal processing means in use receives and processes said first and second signals by analogue processing to produce said output signal as an analogue signal.

* * * * *